(12) United States Patent  
Nadershahi et al.

(10) Patent No.: US 8,985,118 B2
(45) Date of Patent: Mar. 24, 2015

(54) RETENTION DEVICE

(71) Applicant: Alfred E. Mann Institute for Biomedical Engineering at the University of Southern California, Los Angeles, CA (US)

(72) Inventors: Afshin Nadershahi, Northridge, CA (US); Ricardo G. Hahn, Ojai, CA (US)

(73) Assignee: Alred E. Mann Institute for Biomedical Engineering at the University of Southern California, Los Angeles, CA (US)

(*) Notice: Subject to any disclaimer, the term of this patent is extended or adjusted under 35 U.S.C. 154(b) by 0 days.

(21) Appl. No.: 13/690,732

(22) Filed: Nov. 30, 2012

(65) Prior Publication Data

US 2013/0139831 A1 Jun. 6, 2013

Related U.S. Application Data

(60) Provisional application No. 61/565,734, filed on Dec. 1, 2011, provisional application No. 61/675,643, filed on Jul. 25, 2012.

(51) Int. Cl.
*A61B 19/00* (2006.01)
*A61F 13/00* (2006.01)
(Continued)

(52) U.S. Cl.
CPC .. *A61F 5/37* (2013.01); *A61F 6/202* (2013.01)
USPC .............................. 128/869; 602/57

(58) Field of Classification Search
CPC ................... A61F 13/00072; A61F 13/00076;
A61F 13/0008; A61F 13/025; A61F 13/0259;
A61F 13/0269; A61F 15/001; A61F 15/002;
A61F 5/3761; A61F 5/40; A61F 5/37; A61F 6/202
USPC ......... 128/842, 869, 876, 877, 892, 845, 846;
602/60, 61, 67, 70, 71, 41–43, 52–56,
602/79, 63, 900, 901; 600/38, 39, 41;
206/438, 440, 441, 229, 230;
427/2.1–2.31
See application file for complete search history.

(56) References Cited

U.S. PATENT DOCUMENTS

| 4,378,010 A | 3/1983 | McDonald |
| 4,807,753 A * | 2/1989 | Goldstein ..................... 206/390 |

(Continued)

OTHER PUBLICATIONS

International Search Report and Written Opinion of the International Searching Authority, dated Mar. 26, 2013, for PCT Application PCT/US2012/067442, filed Nov. 30, 2012, entitled "Retention Device."

*Primary Examiner* — Alireza Nia
*Assistant Examiner* — Raymond E Harris
(74) *Attorney, Agent, or Firm* — McDermott Will & Emery LLP

(57) ABSTRACT

This application presents retention devices that afford the user quick and easy placement. These retention devices may accommodate objects of various shapes and sizes. The device provides sturdy means for retaining and securing an object to a surface without the need to handle and position flaps of tape. The device allows easy removal from the retained object without adhesives directly contacting or damaging it sensitive surfaces. The retention described here may be used to quickly secure anatomic structures during operations, such as securing the penis against the abdomen during vasectomy, without causing discomfort or damage to sensitive skin during application or removal.

19 Claims, 13 Drawing Sheets

(51) Int. Cl.
*A61F 15/00* (2006.01)
*A61F 5/37* (2006.01)
*A61F 6/20* (2006.01)

(56) References Cited

U.S. PATENT DOCUMENTS

| | | | |
|---|---|---|---|
| 4,858,604 A * | 8/1989 | Konishi | 602/57 |
| 4,928,680 A * | 5/1990 | Sandbank | 602/57 |
| 4,993,586 A * | 2/1991 | Taulbee et al. | 221/25 |
| 5,183,460 A * | 2/1993 | Scherz | 602/79 |
| 5,397,297 A * | 3/1995 | Hunter | 602/54 |
| 5,891,078 A * | 4/1999 | Turngren et al. | 602/58 |
| 5,935,091 A | 8/1999 | Friedman | |
| 7,568,580 B2 * | 8/2009 | Fenton | 206/390 |
| 7,683,235 B2 * | 3/2010 | Wendorf | 602/57 |
| 7,753,204 B2 * | 7/2010 | Grossman | 206/440 |
| 8,398,615 B2 * | 3/2013 | Torstensen et al. | 604/544 |
| 2008/0108864 A1 | 5/2008 | Girgen et al. | |
| 2010/0170912 A1 * | 7/2010 | Grossman | 221/34 |
| 2010/0204626 A1 | 8/2010 | Lemond | |

* cited by examiner

RETENTION DEVICE

CROSS-REFERENCE TO RELATED APPLICATIONS

This application is based upon and claims priority to U.S. Provisional Application Ser. No. 61/565,734, filed Dec. 1, 2011, entitled "Penile Retractor" and U.S. Provisional Application Ser. No. 61/675,643, filed Aug. 2, 2012, entitled "Retention Device". The entire content of these applications are incorporated herein by reference.

BACKGROUND

1. Field

This application relates generally to adhesive tapes, including those used in medical examinations and operations.

2. General Background and State of the Art

When objects need to be rapidly secured and retained in fixed positions, or when surfaces need to be quickly covered or have pressure applied to them, adhesive tapes and bandages are commonly used.

Several methods of deploying and fastening tapes and bandages are available in the market today. Use of adhesive tape alone to secure a three-dimensional structure to a surface may result in damage to the structure upon removal of the adhesive tape.

Furthermore, use of tapes and bandages to quickly secure three-dimensional structures to a surface frequently results in tenting of the tape or bandage, leading to inexact positioning and loosening retention.

Additionally, exposing adhesive surfaces and applying them to their target surface often requires more than one action by the user, including the sometimes cumbersome positioning of loose flaps of tape.

These issues can be especially problematic in medical applications of tapes and bandages to retain structures to skin surfaces. When rapidity is favored, plain tapes are often used, which can cause discomfort or even trauma upon removal from sensitive skin. Furthermore, use of tapes or simple bandages can lead to inexact positioning and loosening retention, which can be problematic during delicate procedures.

For example, during some medical examinations and surgeries involving the male genitalia and surrounding structures (such as in vasectomy, urology-related, and colorectal surgeries), the patient's penis is pulled over the lower abdomen or to the side of the thigh of the patient and typically secured by tape to provide the surgeon access to the genitalia and surrounding structures. On completion of the procedure, the tape is removed from the penis.

However, use of medical adhesive tape to retain the penis to the lower abdomen or thigh causes several complications. Firstly, the penis skin is very sensitive and prone to being pulled and stretched during removal of the tape, causing considerable discomfort and in some cases skin damage to the patient. Secondly, in order to avoid inflicting discomfort or skin damage to the penis, the user has to take special care while removing the tape making the process time consuming. In addition, the user may apply several pieces of tape to stabilize the penis, further aggravating the discomfort and skin damage to the patient during removal of the pieces of tape.

SUMMARY

This disclosure provides retention devices that may be quickly and easily applied to retain variety of objects on different surfaces. These retention devices may accommodate objects of various shapes and sizes.

Firstly, the retention device may provide sturdy means for retaining and securing an object to a surface without the need to handle and position flaps of tape.

Secondly, the retention device may allow easy removal from the retained object without adhesives directly contacting or damaging its sensitive surfaces.

The retention device described here may be used to quickly secure anatomic structures during operations, such as securing the penis against the abdomen during vasectomy, without causing discomfort or damage to sensitive skin during application or removal.

The retention device may comprise at least one enclosure, at least one channel, at least one opening, at least one adhesive film, and at least one tab. In one exemplary embodiment, the at least one enclosure may comprise at least one outer casing and at least one inner casing. The inner casing may have an exterior surface and an interior surface. The outer casing may have an exterior surface and an interior surface. The exterior surface of the inner casing may face the interior surface of the outer casing. The at least one channel may be located between the outer casing and the inner casing. The at least one adhesive film may be located between the at least one outer casing and the at least one inner casing. The at least one tab may be located between the at least one outer casing and the at least one adhesive film.

The retention device may further comprise at least one tab that may have a portion that may protrude out of the at least one opening. This portion of the at least one tab may attach to a portion of the at least one adhesive film. Another portion of the at least one tab may be placed between the at least one outer casing and the at least one inner casing. Another portion of the at least one adhesive film may be attached to the at least one inner casing.

The at least one adhesive film may comprise at least one backing and at least one adhesive layer. A portion of the at least one adhesive layer may be located between the at least one outer casing and the at least one backing. A portion of the at least one tab may be located between the at least one outer casing and the at least one adhesive layer.

In one embodiment, the at least one outer casing and the at least one inner casing may form an arch.

The at least one opening may be located between the at least one outer casing and the at least one inner casing. The at least one opening may also be located on the exterior surface of the at least one outer casing. The retention device may further comprise at least two openings.

In another embodiment, the at least one inner casing may comprise at least one inner casing protrusion.

The retention device further may further comprise at least one padding. The padding may be a medical padding. The medical padding may comprise a chemical useful for managing or healing the wound.

The retention device may further comprise at least two tabs.

The retention device may further comprise at least one marking line. The at least one marking line may be placed on the exterior surface of the at least one inner casing.

The retention device may further comprise at least one pliable sheet. The at least one pliable sheet may span across the space underneath the arch formed by the at least one enclosure.

In one embodiment, the at least one adhesive film may be attached to the interior surface of the inner casing.

In another embodiment, the retention device may have a grip texture. This grip texture may be formed on the exterior surface of the outer casing.

The at least one tab may further comprise an imprinted instruction.

The at least one inner casing and the at least one outer casing may be both flexible. They may also be both rigid.

In one embodiment, the at least one adhesive film may be configured to fold over itself when the retention device is not deployed and to unfold when the retention device is deployed.

It is understood that other embodiments of the devices and methods will become readily apparent to those skilled in the art from the following detailed description, wherein only exemplary embodiments of the devices, methods and systems are shown and described by way of illustration. As will be realized, the devices and systems are capable of other and different embodiments and their several details are capable of modification in various other respects, all without departing from the spirit and scope of the invention. Accordingly, the drawings and detailed description are to be regarded as illustrative in nature and not as restrictive.

BRIEF DESCRIPTION OF THE DRAWINGS

Aspects of the retention device are illustrated by way of example, and not by way of limitation, in the accompanying drawings, wherein.

DETAILED DESCRIPTION

The detailed description set forth below in connection with the appended drawings is intended as a description of exemplary embodiments and is not intended to represent the only embodiments in which the retractors can be practiced. The term "exemplary" used throughout this description means "serving as an example, instance, or illustration," and should not necessarily be construed as preferred or advantageous over other embodiments. The detailed description includes specific details for the purpose of providing a thorough understanding of the retractors. However, it will be apparent to those skilled in the art that the retractors and may be practiced without these specific details.

The device may comprise at least one enclosure, at least one tab, at least one opening, at least one channel, and at least one adhesive film. The enclosure may comprise at least one outer casing and at least one inner casing. The inner casing has an exterior surface and an interior surface. The outer casing has an exterior surface and an interior surface. The exterior surface of the inner casing faces the interior surface of the outer casing, when the device is assembled. In one embodiment, the at least one opening may be formed through the outer casing. In another embodiment, the at least one opening may be formed through the inner casing. In yet another embodiment, the at least opening may be formed through both the inner casing and the other casing.

The channel may be between the outer casing and the inner casing. The at least one adhesive film may be located between the at least one outer casing and the at least one inner casing. The at least one tab may be located between the at least one outer casing and the at least one adhesive film. In one embodiment, the inner casing may further comprise at least one protrusion. In another embodiment, the inner casing may further comprise at least one marking line. In yet another embodiment, the device may further comprise at least one padding.

Figure 1:
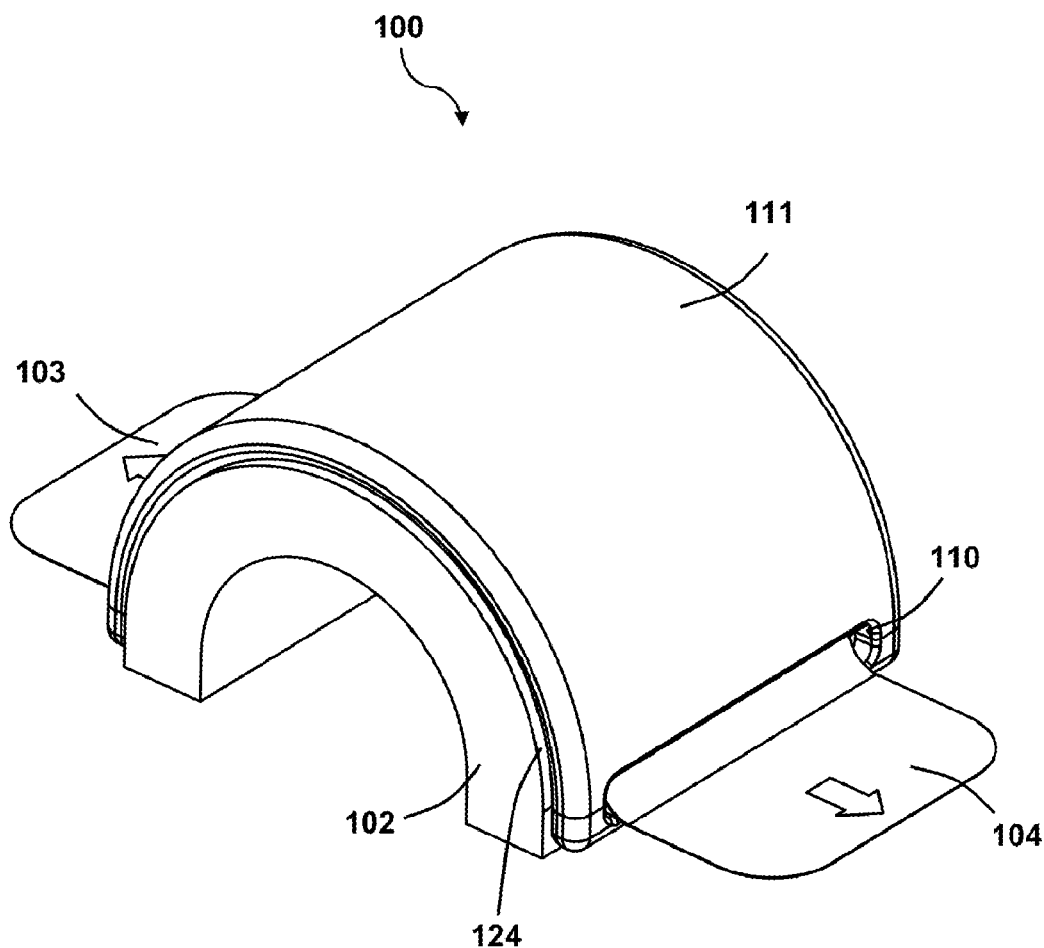
FIG. 1 is an isometric view of an exemplary retention device.
Figure 2:
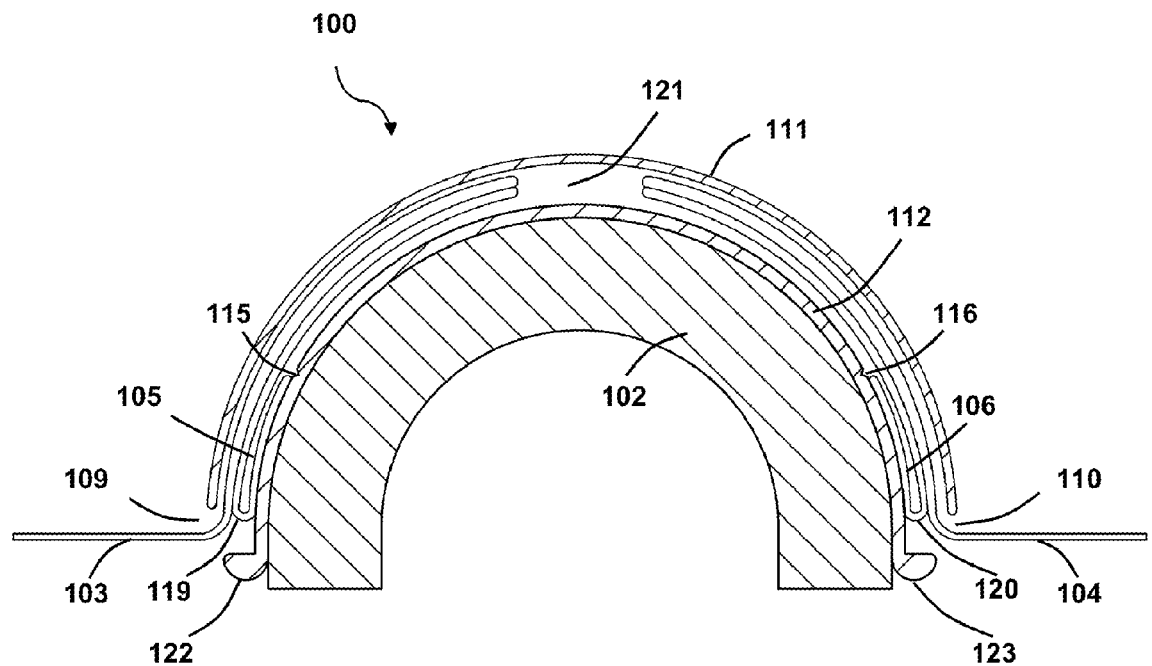
FIG. 2 is a cross-section view of the exemplary retention device of FIG. 1.
Figure 3:
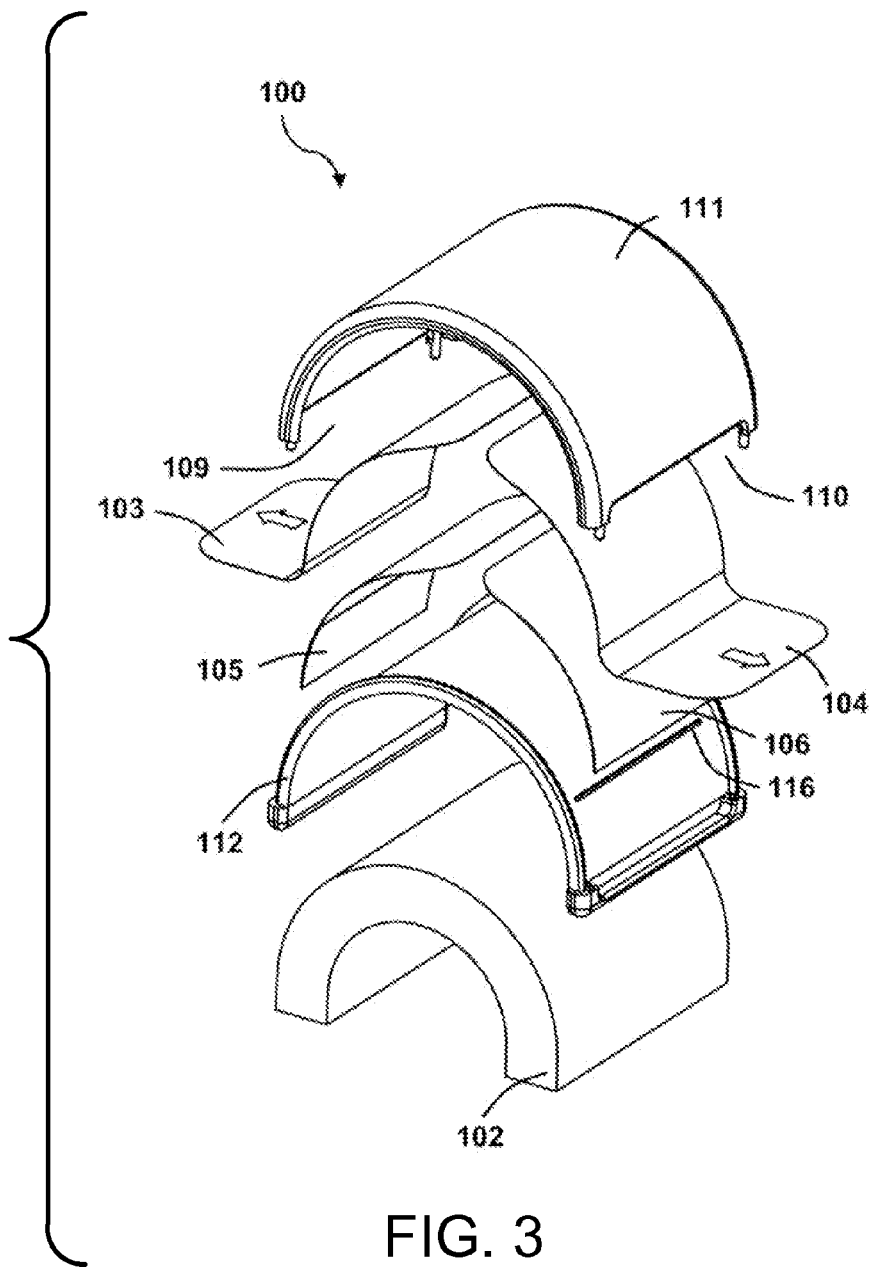
FIG. 3 is an isometric exploded view of the exemplary retention device of FIG. 1.

FIGS. 1-3 depict an exemplary retention device 100, which comprises an outer casing 111, an inner casing 112, tabs 103 and 104, openings 109 and 110, a channel 121, adhesive films 105 and 106, inner casing protrusions 122 and 123, marking lines 115 and 116 and a padding 102. The adhesive film comprises a backing and an adhesive layer (not shown separately in the figures). The backing may be non-adhesive.

As shown in FIGS. 2-3, each adhesive film may be attached at one end to a lateral edge of the inner casing 112, and folded back upon itself 119 or 120 at this lateral edge such that the remaining adhesive surface faces up within the channel 121 facing the interior surface of the outer casing. The tabs 103 and 104 may extend into the channel 121 through openings 109 and 110 on each end, as shown in FIGS. 1-3, and cover the remaining adhesive surface that face up within the channel 121. Therefore, pulling on the tabs 103 and 104 may pull the adhesive films 105 and 106 out from the channel 121. This pulling action may peel the tabs 103 and 104 off of the adhesive films 105 and 106, thus exposing the adhesive films' adhesive layer.

Figure 4:
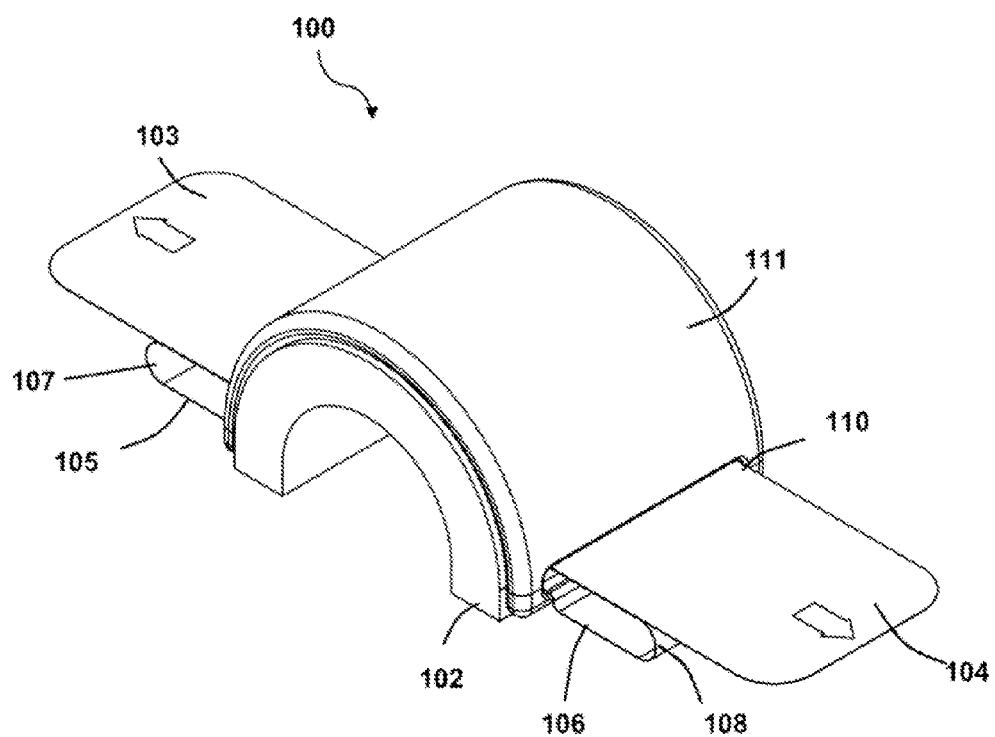
FIG. 4 is an isometric view of the exemplary retention device of FIG. 1, with the pull-tabs pulled laterally and the adhesive tape partially deployed.
Figure 5:
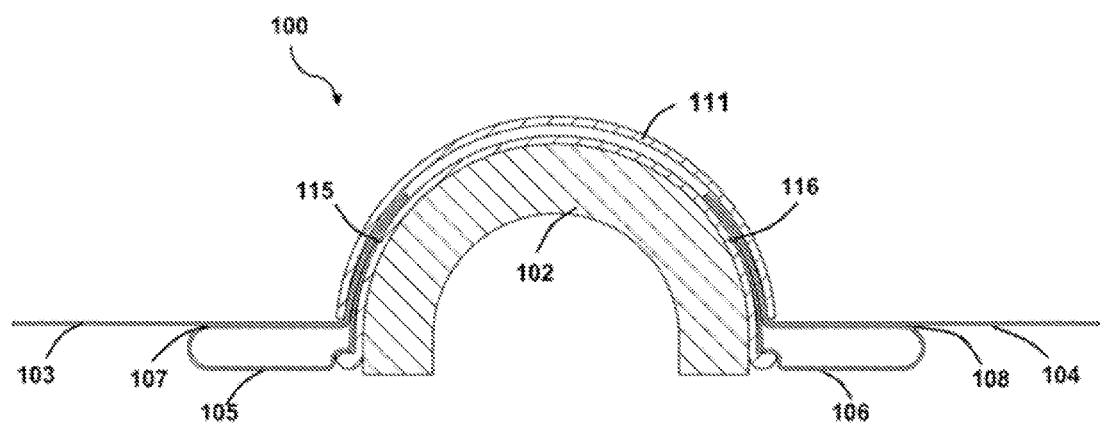
FIG. 5 is a cross-section view of the exemplary retention device of FIG. 1, with the pull-tabs pulled laterally and the adhesive tape partially deployed.
Figure 6:
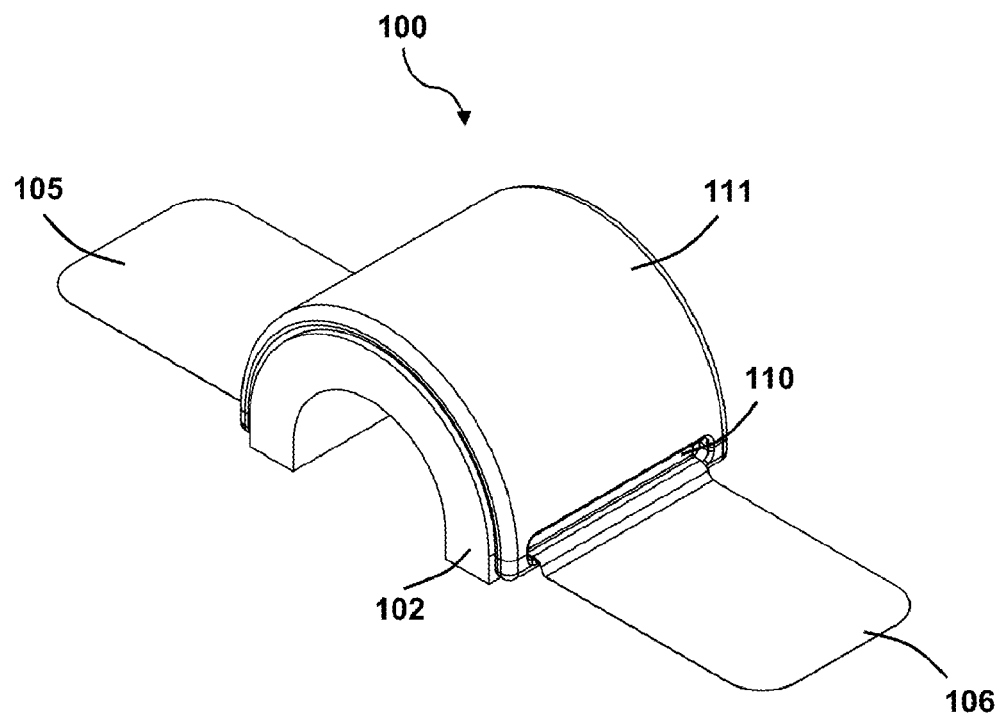
FIG. 6 is an isometric view of the exemplary retention device of FIG. 1, with the pull-tabs removed and the adhesive tape fully deployed.
Figure 7:
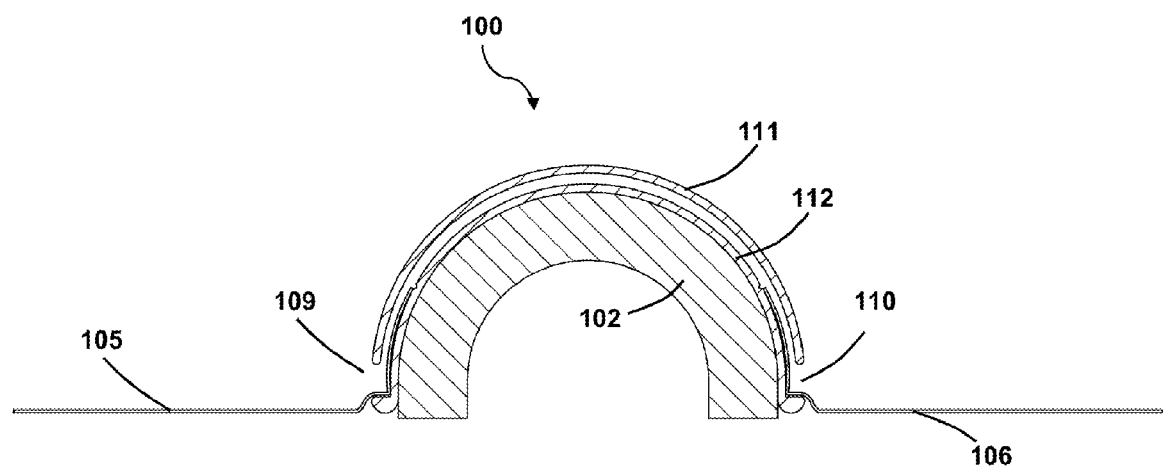
FIG. 7 is a cross-section view of the exemplary retention device of FIG. 1, with the pull-tabs removed and the adhesive tape fully deployed.

FIGS. 4-7 depict views of the retention device 100, when the adhesive films 105 and 106 are simultaneously deployed and applied to a surface. FIGS. 4-5 illustrate unfurled and separated portions 107 and 108 of the adhesive films 105 and 106 from the tabs 103 and 104. The resulting adhesion of the adhesive films 105 and 106 to an underlying surface may indirectly hold the device 100 onto whatever structure is retained underneath it. FIG. 6-7 depict views of the exemplary retention device 100 with tabs fully removed and adhesive films 105 and 106 fully deployed with their adhesive layers facing down and applied to the underlying surface. (The underlying surface is not shown in the figures.)

The outer casing 111 and the inner casing 112 may have various properties to accommodate the object retained underneath under desired conditions. These properties may include rigidity, softness, opacity, transparency, breathability, water-resistance, elution of chemicals, or specific contours to accommodate certain objects or anatomical shapes. In some embodiments, these casings may be flat. The casings 111 and 112 may be rigid, and may comprise plastic, rigid foam, metal, or other materials with sufficient rigidity and durability to securely retain an object positioned underneath the inner casing. Alternatively, the casings may be flexible, and may comprise thin plastic, soft metal, or other materials. In another embodiment, the casings may be constructed from a semi-rigid, shape-retaining material; this shape-retaining material could provide means for the user to manipulate the shape of the casing to conform to the shape of the structure that needs retaining. The casings may comprise a non-continuous surface. For example, the casings may be constructed as a frame; this frame may comprise a plurality of ribs or rings separated along the length of the casings.

The inner casing 112 may provide a structure to which padding 102 may attach. This padding 102 may be affixed to the underside of the inner casing 112 so that it contacts the retained object, providing a soft contact surface. In some instances, this padding 102 may serve as a comfortable contact surface when applied to skin. Additionally, the padding 102 may serve as a non-slip surface to prevent the retained object from sliding out from under the device once it has been secured. Furthermore, in some embodiments, the compressive nature of the padding 102 may permit the retention of a range of object sizes. Furthermore, the padding may be absorptive or chemical-eluting. As depicted in FIG. 1, the padding 102 edges may extend beyond edges of the casings 111 and 112 to form padding overhangs 124. When the device is applied to the retained object, these padding overhangs may prevent the retained object from coming in direct contact with the casings 111 and 112. Alternatively, the casings themselves may comprise a compliant material, such as foam or cloth, with any of the aforementioned properties.

Figure 8:
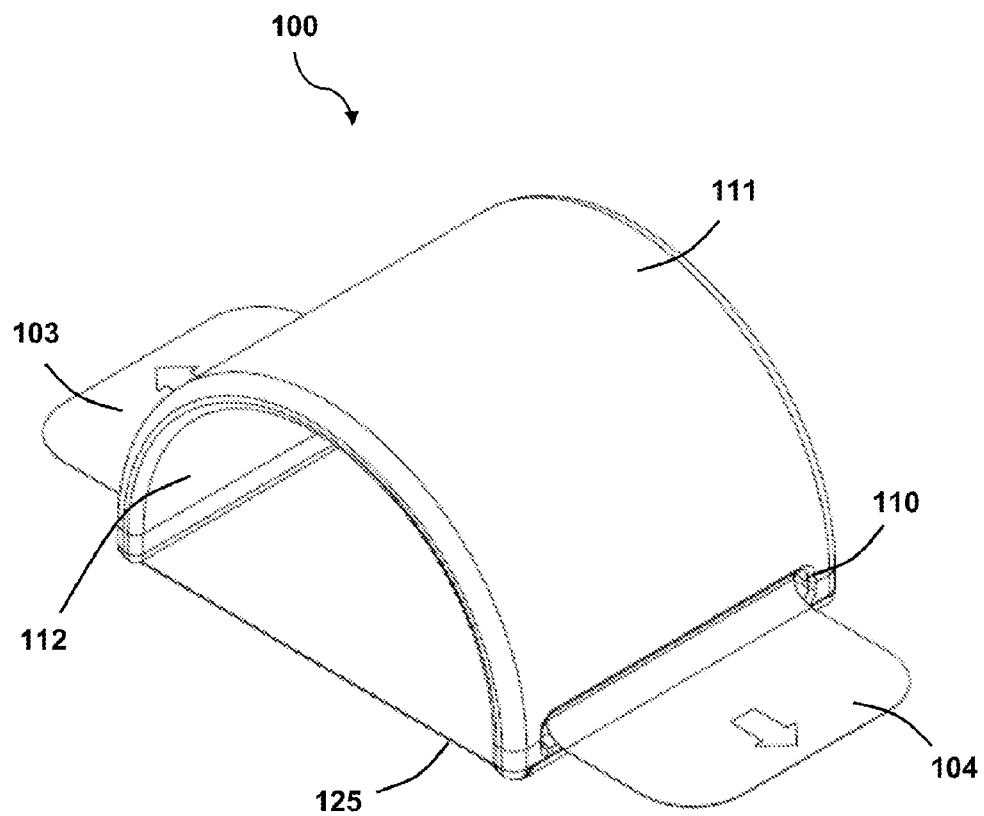
FIG. 8 is an isometric view of an exemplary retention device.
Figure 9:
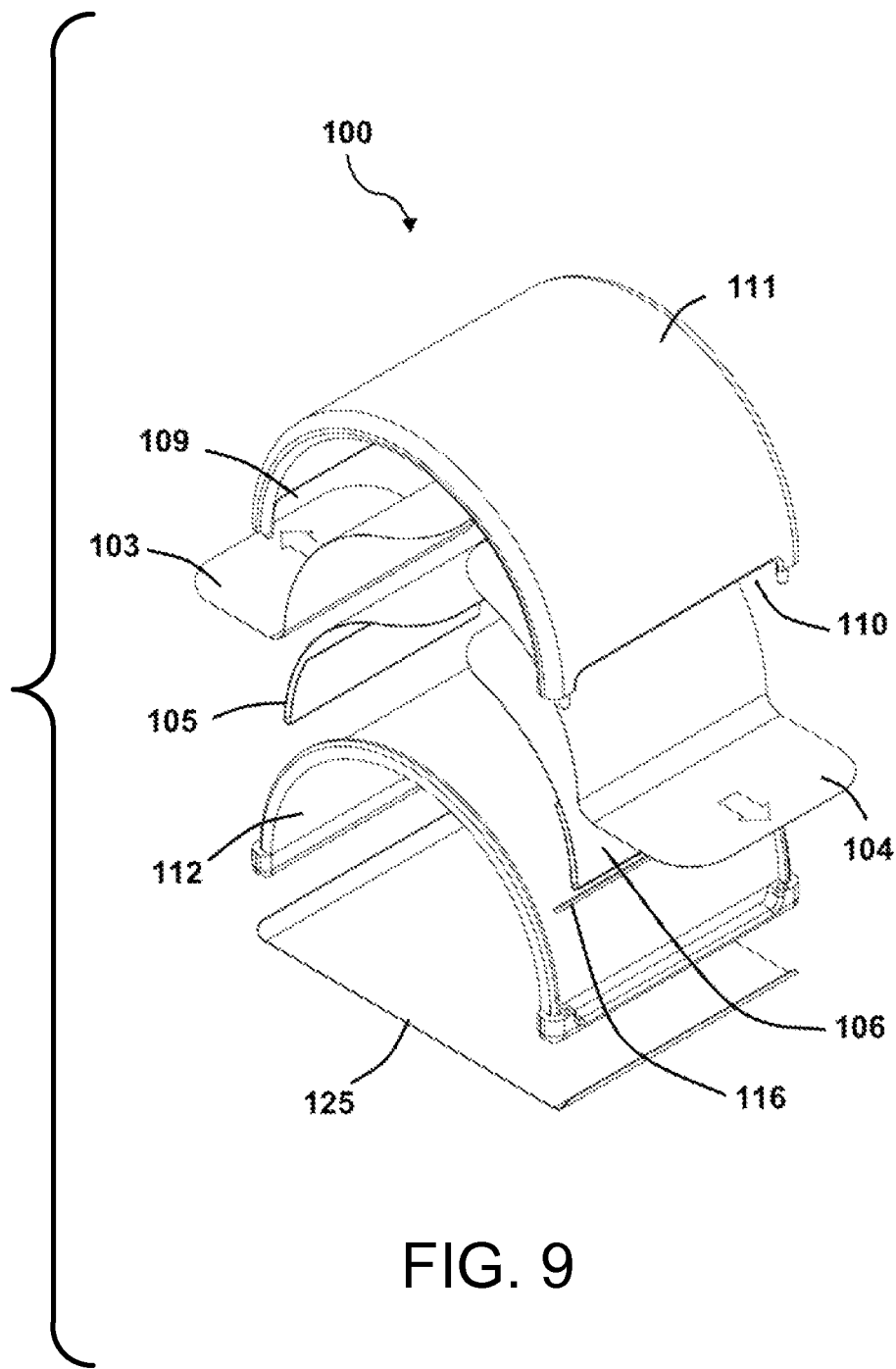
FIG. 9 is an isometric exploded view of the exemplary retention device of FIG. 8.

In another embodiment, a pliable sheet 125 may span the space underneath the arch, forming a stretchable strap that accommodates objects of different shapes and/or sizes, as shown in FIGS. 8-9. Examples of the pliable sheet 125 may be a cloth or flexible polymer film. In this embodiment, there is no padding. When the retention device of this embodiment is deployed, the pliable sheet 125 conforms to the objects retained underneath.

In one embodiment, the adhesive films 105 and 106 may each be attached at one end of the inner casing 112, and may be concealed within the channel 121 until pulled out by pulling on the tabs 103 and 104. The adhesive films 105 and 106 may be any adhesive film. For example, adhesive tape, bandage and wound dressing.

The adhesive layer of the adhesive film 105 and 106 may comprise any adhesive, for example, pressure sensitive adhesives, reversible adhesives, heat sensitive adhesives and water activated adhesives. The adhesive layer may be covered by tabs 103 and 104. These tabs 103 and 104 may comprise a non-adhesive material to prevent unintentional adhesion with surfaces of the device itself, the user, or other surfaces.

Figure 10:
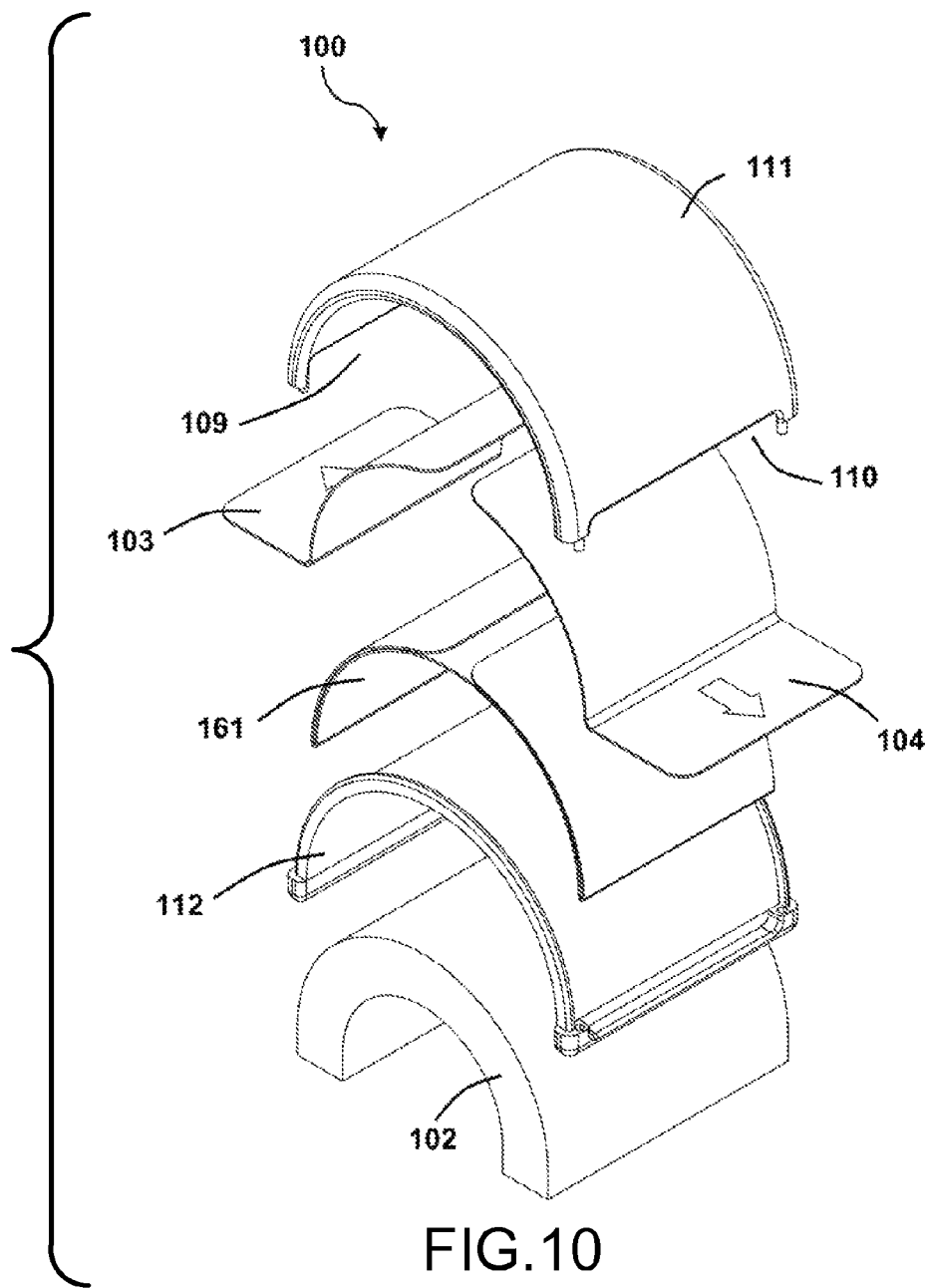
FIG. 10 is an isometric exploded view of an exemplary retention device.
Figure 11:
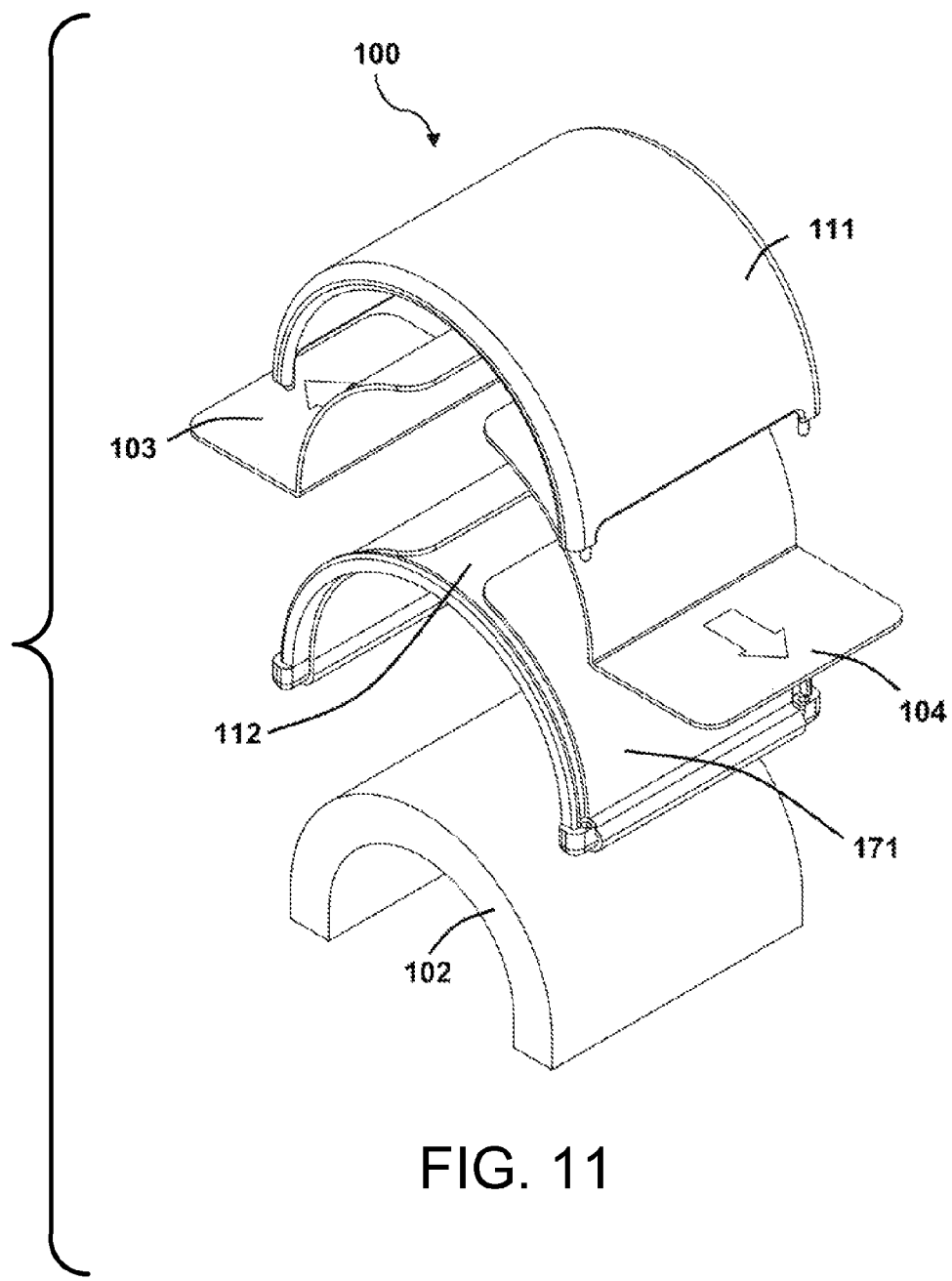
FIG. 11 is an isometric exploded view of an exemplary retention device.

In an alternative embodiment, there may be one adhesive film 161 extending over the exterior surface of the inner casing, as shown in FIG. 10. In an alternative embodiment, there may be one adhesive film 171 extending over both the exterior surface of the inner casing and interior surface of the inner casing, as shown in FIG. 11.

In one embodiment, depicted in FIG. 1-11, the casings 111 and 112 may comprise an arch. The arch may have any shape suitable for the application. For example, the arch may be circular, elliptical, oval or rectangular. The diameter of circular arch can be any diameter suitable for a particular application. In an exemplary embodiment of a circular arch, the diameter may range from 20 mm to 100 mm, while the length of the arch may range from 20 mm to 100 mm. In an exemplary embodiment, both casings 111 and 112 may have same dimensions. For example, the dimensions of both casings 111 and 112 may be as follows: the diameter is about 55 mm, and the length is about 55 mm. As an example, the channel 121 is about 2 mm high and about 50 mm wide.

FIG. 3 depicts an isometric exploded view of an exemplary device. The inner casing 111 and the outer casing 112 together form the channel 121 with an opening on each of the devices two openings 109 and 110. In the embodiment depicted in FIG. 3, the outer casing 111 is attached to the inner casing 112; the resulting enclosure houses the adhesive films 105 and 106 until they are deployed.

In another embodiment, the device may further comprise marking lines 115 and 116 on the exterior surface of the inner casing 112 to facilitate positioning and alignment of the adhesive films 105 and 106. The marking line may be located on the exterior surface of the inner casing. Examples of the marking line are a groove, a protrusion, and an imprinted ink line and combinations thereof.

Referring to FIGS. 1-6, in an exemplary method of applying the device, the user may first apply the device 100 onto the object to be retained, then may pull on the two tabs either one-at-a-time or simultaneously to deploy and adhere the adhesive films 105 and 106 to the underlying surface.

In yet another exemplary embodiment (not shown in the figures), the device may comprise one enclosure, one tab, one opening, a channel, one adhesive film, one inner casing protrusion, one marking line and a padding. The enclosure of this device may further comprise at least one outer casing and at least one inner casing. The channel of this device may be placed between the at least one outer casing and the at least one inner casing. This configuration may render the device suitable for hanging from a surface such as a wall. The casings may comprise an arch. The arch may have any shape suitable for the application. For example, the arch may be circular, elliptical, oval, or rectangular. The diameter of circular arch can be any diameter suitable for a particular application. In another embodiment, the casings may be in the shape of a hook, such that the device may function as a hook that is easily adhered to a surface such as a wall. In another embodiment, the device may provide means for attaching other objects, such as hooks or adhesive surfaces on the exterior surface of the outer casing.

In another exemplary embodiment, the exterior surface of the outer casing has texture to improve gripping or reduce slipping of the retention device while it is being handled or deployed. Examples of this grip texture are knurled patterns, irregular textures formed by sand blasting, grooves, ridges or combinations thereof.

In another exemplary embodiment, the tabs may have instructions imprinted on their surface to indicate the pulling direction of the tabs. These instructions may be in the form of symbols, texts or combinations thereof. An example of a symbol may be an arrow, as illustrated in FIGS. 1 and 9-11.

The retention device in one embodiment may be for penile retraction. The retention device may be particularly well suited for penile retraction during vasectomy, because it may facilitate quick securement of the penis to the abdomen without direct contact of an adhesive substance to the sensitive skin of the penis. Firstly, the device may provide a sturdy means for retaining and securing the patient's penis onto the lower abdomen or side of the thigh, giving the surgeon a clear and unobstructed view of the scrotum and surrounding structures. Secondly, the device may allow easier removal from the patient's penis without causing discomfort or skin damage to the sensitive penis skin.

The retention device in one embodiment may be for affixing a padding on top of an open wound. In this embodiment, the padding may comprise a medical padding that provides healing. Examples of such paddings may be gauzes, dressings, sponges, hydrogels and combinations thereof. The medical padding may comprise a chemical useful for wound healing or management. An example of such chemical is a silver compound such as silver nitrate.

The previous description of the disclosed embodiments is provided to enable any person skilled in the art to make or use the retention devices. Various modifications to these embodiments will be readily apparent to those skilled in the art, and the generic principles defined herein may be applied to other embodiments without departing from the spirit or scope of the retainers. Thus, the retaining devices are not intended to be limited to the embodiments shown herein but are to be accorded the widest scope consistent with the principles and novel features disclosed herein.

Figure 12:
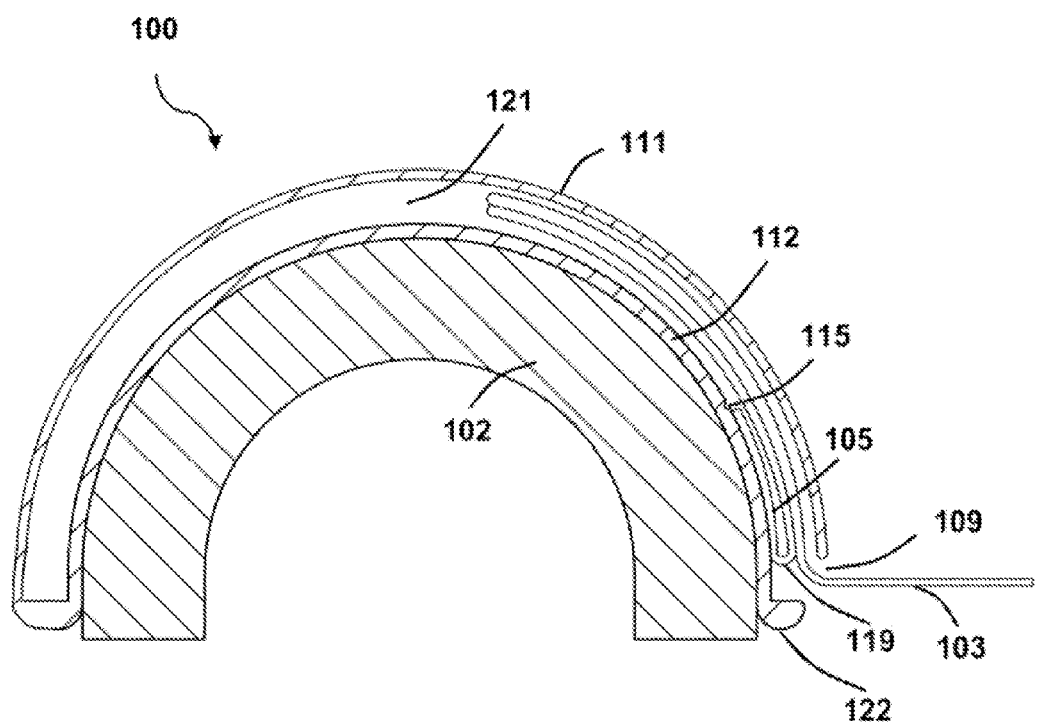
FIG. 12 illustrates a cross-section view of an exemplary device.
Figure 13:
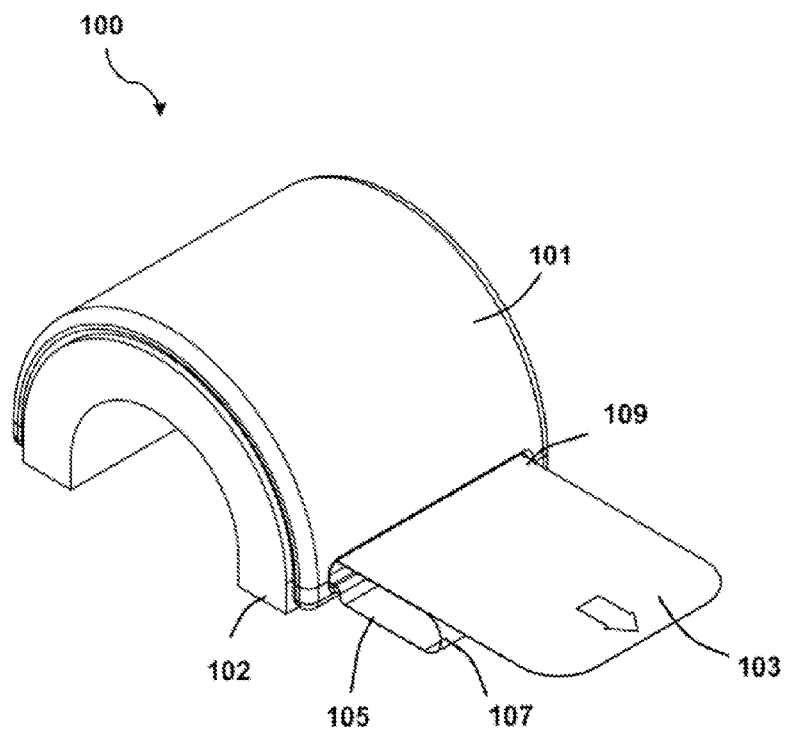
FIG. 13 illustrates an isometric view of the exemplary retention device of FIG. 12, with the pull-tab pulled laterally and the adhesive tape partially deployed.

FIGS. 12-13 depict another exemplary retention device 100, which comprises an outer casing 111, an inner casing 112, a tab 103, an opening 109, a channel 121, an adhesive film 105, an inner casing protrusion 122, a marking line 115, and a padding 102.

We claim:

1. A retention device comprising:
an enclosure, wherein the enclosure comprises an outer casing and an inner casing;
wherein the inner casing has an exterior surface and an interior surface, wherein the outer casing has an exterior surface and an interior surface, wherein the exterior surface of the inner casing faces the interior surface of the outer casing;
a channel located between the outer casing and the inner casing;
one or two openings;
one or two adhesive films, each having an adhesive layer; and
one or two tabs;
wherein each adhesive film is located between the outer casing and the inner casing;
wherein an end of the adhesive layer of each adhesive film is directly attached to the exterior surface of the inner casing;
wherein each tab is located between the outer casing and the adhesive films;
wherein the retention device has a configuration that retains an object underneath the inner casing without having direct contact of an adhesive layer with the object when the retention device is deployed;
wherein each adhesive film extends away laterally from the inner casing when the retention device is deployed; and
wherein adhesion of each adhesive film to an underlying surface holds the retention device onto the object underneath the inner casing when the retention device is deployed.

2. The retention device of the claim 1, wherein the outer casing and the inner casing each form an arch that spans across openings at each end of the arch.

3. The retention device of the claim 2, wherein each opening is located on the exterior surface of the outer casing.

4. The retention device of the claim 3, wherein the inner casing comprises at least one inner casing protrusion.

5. The retention device of the claim 2, wherein the retention device further comprises a pliable sheet, wherein the pliable sheet spans across space underneath the arch.

6. The retention device of the claim 1, wherein the retention device further comprises a padding.

7. The retention device of the claim 6, wherein the padding is a medical padding.

8. The retention device of the claim 7, wherein the medical padding comprises a chemical useful for managing or healing a wound.

9. The retention device of the claim 1, wherein a portion of each tab protrudes out of one of the openings.

10. The retention device of the claim 1, wherein a portion of each tab is attached to a portion of one of the adhesive films.

11. The retention device of the claim 1, wherein a portion of each tab is placed between the outer casing and the inner casing.

12. The retention device of the claim 1, wherein each opening is located between the outer casing and the inner casing.

13. The retention device of the claim 1, wherein the inner casing further comprises a marking line.

14. The retention device of the claim 1, wherein the exterior surface of the outer casing has a grip texture.

15. The retention device of the claim 1, wherein each tab further comprises an imprinted instruction.

16. The retention device of the claim 1, wherein the inner casing and the outer casing are both flexible.

17. The retention device of the claim 1, wherein the inner casing and the outer casing are both rigid.

18. The retention device of the claim 1, wherein each adhesive film is configured to fold over itself when the retention device is not deployed and to unfold when the retention device is deployed.

19. The retention device of the claim 1, wherein the retention device comprises two openings and two tabs; and wherein one tab is at one opening and the other tab is at the other opening, and wherein the retention device is configured to permit the one tab that is at one opening and the one other tab that is at the other opening to move in opposite directions in response to opposing pulling forces that are applied to the two tabs.

* * * * *